United States Patent [19]

Norris

[11] Patent Number: 4,529,801
[45] Date of Patent: Jul. 16, 1985

[54] PRIMARY EXPLOSIVE

[75] Inventor: William P. Norris, Ridgecrest, Calif.

[73] Assignee: The United States of America as represented by the Secretary of the Navy, Washington, D.C.

[21] Appl. No.: 555,775

[22] Filed: Nov. 28, 1983

[51] Int. Cl.³ .................................................. C07D 271/08
[52] U.S. Cl. ........................................ 548/126; 149/88
[58] Field of Search ........................................ 548/126

[56]  References Cited
PUBLICATIONS

Spear et al., Rep.–Mater. Res. Lab. (Aust.), MRL–R–881 (1983).
Norris et al., Rep.–Mater. Res. Lab. (Aust.), MRL–8–870 (1983).

Primary Examiner—Robert Gerstl
Attorney, Agent, or Firm—Robert F. Beers; W. Thom Skeer; Shelley G. Precivale

[57] ABSTRACT

A primary explosive, potassium 7-hydroxyamino-4,6-dinitro-4,7-dihydrobenzofuroxanide

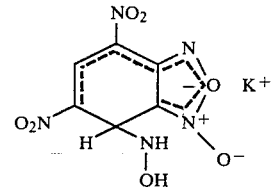

is prepared by reacting 4,6-dinitrobenzofuroxan with hydroxylamine in a methanolic solution of potassium bicarbonate.

4 Claims, No Drawings

PRIMARY EXPLOSIVE

BACKGROUND OF THE INVENTION

1. Field of the Invention

This invention relates to explosives. More particularly, this invention relates to a primary explosive.

2. Description of the Prior Art

Explosives are categorized as primary, secondary or high explosives in order of decreasing sensitivity to energy input. Primary or initiator explosives are the most sensitive to mechanical, electrostatic and thermal stimulae. Primary explosives are powders with good flow transfer and pressing characteristics to allow for high speed automatic loading of detonators. Some primary explosives are used in non-detonating stab and percussion primers to accomplish mechanical work or to initiate burning actions.

Two common components of explosive initiators are lead azide and tetrazene, but both have detrimental properties. Lead azide contains the toxic heavy metal and is hydrolytically unstable. The hydrazoic acid formed in the presence of moisture can react with the brass fuze fittings of military ordnance to form the dangerously sensitive cupric azide. Tetrazene suffers from a low ignition temperature of 140° C. and is only marginally satisfactory.

Potassium dinitrobenzofuroxan (KDNBF) or potassium 4,7-dihydro-4,6-dinitrobenzofuroxan-7-ol is the potassium salt or Meisenheimer complex formed when 4,6-dinitrobenzofuroxan is dissolved in aqueous potassium bicarbonate. KDNBF has found use in primary explosive compositions. The sodium, silver, cesnium and rubidium salts are also known.

SUMMARY OF THE INVENTION

This invention provides the compound, potassium 7-hydroxyamino-4,6-dinitro-4,7-dihydrobenzofuroxanide, useful as a primary explosive.

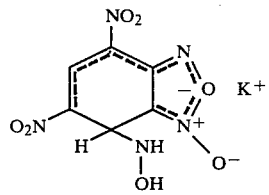

The method of making the compound comprises the reaction of 4,6-dinitrobenzofuroxan with hydroxylamine in the presence of potassium bicarbonate at a temperature of 10°-50° C. to produce free flowing small spherical crystals.

OBJECTS OF THE INVENTION

It is an object of this invention to provide a novel primary explosive useful as an initiator or as a component in an initiator for detonating a train of secondary explosives.

Another object of the invention is to provide a method of making the compound.

These and other objects of the invention will become more readily apparent from the following detailed description.

DESCRIPTION OF THE PREFERRED EMBODIMENT

Potassium 7-hydroxyamino-4,6-dinitro-4,7-dihydrobenzofuroxanide readily forms in nearly quantitative yield from reaction of 4,6-dinitrobenzofuroxan with hydroxylamine in the presence of a methanolic solution of potassium bicarbonate. The product is isolated as free flowing nearly spherical crystals. The reaction can be carried out at a temperature of 10°-50° C. without significant variation in yield. However, a preferred temperature of 40° C. produced the most uniform particle size and contained no unreacted 4,6-dinitrobenzofuroxan.

The following example illustrates the preparation and analysis of the compound. The analysis and properties were all obtained following procedures familiar to anyone skilled in the art of chemistry and explosives.

EXAMPLE 1

4,6-dinitrobenzofuroxan (2.00 g, 8.85 mmol) was added in one portion to a well stirred solution of hydroxyammonium chloride (0.614 g, 8.84 mmol) in methanol (100 ml) at 50° C. Stirring was continued until dissolution was complete (approx. 20 minutes), then the solution was allowed to cool to 40° C. A solution of potassium bicarbonate in methanol (0.30M, 59 ml) warmed to about 40° C. was then added in one lot with stirring. The solution turned deep red-brown and commenced precipitation of a red product almost immediately. Stirring was continued for 30 minutes at 25° C. and the reaction mixture became more red in color. After cooling to room temperature, the product was isolated by filtration under suction, washed with cold methanol (20 ml) and air-dried. The product, potassium 7-hydroxyamino-4,6-dinitro-4,7-dihydrobenzofuroxanide, was obtained as small, almost spherical, free flowing dark red crystals (2.52 g, 96% yield); m.p. begins at 165° C. with gas evolution.

Analysis

Anal. calcd. for $C_6H_4N_5O_7K$: C, 24.24; H, 1.36; N, 23.56; K, 13.14. Found: C, 24.24; H, 1.51; N, 23.43; K, 12.93.

IR(KBr): 3440, 3270, 1630, 1575, 1550, 1440, 1420, 1395, 1230, 1205, 1155, 1080, 820, 740 $cm^{-1}$.

NMR ($d_6$-DMSO): $\delta 5.27$, d, J=1.5 Hz, H-7; $\delta 8.68$, s, H-5; $\delta 7.49$, d, J-3.1, OH; $\delta 6.03$, broad t, NH.

UV ($CH_3OH$): 466 nm, E=31,300; 356 nm, E=7900; 304 nm, E=12,300; 266 nm, E=13,400.

Density=1.92 g/cc at 25° C.

Impact Sensitivity=11 cm with 2.5 Kg weight (50% point).

Ignition Temperature=152° C.

The ability of the compound to function as an energetic sensitizer was assessed on admixtures with lead azide. Stab initiation energies for 1:10 admixtures (compound:lead azide) and 1:20 admixture are compared below with tetrazene-lead azide mixtures in Table 1. Stab initiation energies for the admixtures are only twice those of the corresponding tetrazene compositions and well within the practical use range.

TABLE 1

| composition | stab initiation energies (50% level, mJ) |
|---|---|
| 1:10 (compound:lead azide) | 6.5-7.6 |
| 1:20 (compound:lead azide) | 9.2 |

TABLE 1-continued

| composition | stab initiation energies (50% level, mJ) |
|---|---|
| 1:10 (tetrazene:lead azide) | 3.3 |
| 1:20 (tetrazene:lead azide) | 3.5 |

Obviously many modifications and variations of the present invention are possible in light of the above teachings. In particular, it is expected that the potassium ion could be replaced by other alkali groups to generate similar exposives. It is therefore to be understood that within the scope of the appended claims, the invention may be practiced otherwise than as specifically described.

What is claimed is:

1. Potassium 7-hydroxyamino-4,6-dinitro-4,7-dihydrobenzofuroxanide.

2. A method of making the compound potassium 7-hydroxyamino-4,6-dinitro-4,7-dihydrobenzofuroxanide comprising the steps of:
   mixing 4,6-dinitrobenzofuroxan and hydroxyammonium chloride in a solvent; and
   reacting said mixture of 4,6-dinitrobenzofuroxan and hydroxyammonium chloride with a methanolic solution of potassium bicarbonate at 10° to 50° C. to form said compound.

3. A method according to claim 2 wherein said solvent is methanol.

4. A method according to claim 2 wherein said solvent is a mixture of methanol and water.